United States Patent [19]

Hein, Jr. et al.

[11] 4,297,885

[45] Nov. 3, 1981

[54] ACOUSTIC EMISSION FOR DETECTION AND MONITORING OF CRACK INITIATION AND PROPAGATION IN MATERIALS

[75] Inventors: Norman W. Hein, Jr.; Donald H. Oertle, both of Ponca City, Okla.

[73] Assignee: Conoco Inc., Ponca City, Okla.

[21] Appl. No.: 87,918

[22] Filed: Oct. 24, 1979

[51] Int. Cl.³ .......................................... G01N 29/04
[52] U.S. Cl. ...................................... 73/587; 73/588
[58] Field of Search ................. 73/587, 588, 582, 583, 73/577; 116/212

[56] References Cited

U.S. PATENT DOCUMENTS 3,774,443 11/1973 Green et al. ........................ 73/587
4,009,463 2/1977 Vercellotti ........................... 73/587

Primary Examiner—Anthony V. Ciarlante
Attorney, Agent, or Firm—Cortlan R. Schupbach, Jr.

[57] ABSTRACT

Initiation and propagation of cracks in materials is detected and monitored by (a) adhering an acoustical emitter to the area of the material to be monitored, and (b) monitoring for acoustical signals emitted by the adhered emitter, said signals produced by cracks in the material initiating in or propagating into the acoustical emitter. An acoustical emitter such as brittle plastic, glass rods or strips and metal such as tin or cadmium can be used.

16 Claims, 4 Drawing Figures

ACOUSTIC EMISSION FOR DETECTION AND MONITORING OF CRACK INITIATION AND PROPAGATION IN MATERIALS

This invention relates to early detection of crack formations in either porous or non-porous materials subject to stress. More specifically, this invention relates to a method for the early detection of crack formation and propagation in these materials through the use of acoustical emitters placed upon the surface to be monitored.

Crack formation in either porous or non-porous materials subject to stress is a problem long recognized and one which has received much attention in recent years. For example, in non-porous materials, formation of cracks in structural members subject to stress is a problem of great importance. This is particularly true in metallic structural members of all configurations wherein crack initiation is but the first step leading to total failure of the members. For example, the frame members of aircraft, frame members of ships, and members of steel offshore production and drilling platforms all depend heavily upon metallic structural components. In the constant search for more efficient structures, additional stress is placed on these structural members which pushes the technology of metallic structural members to the limits of the art of metallurgy and engineering designs involved. In addition to these examples, other uses of solid metallic structural members subject to stress, which are potential hazards to the operational safety of the structures and well being of those using them, include rib frames of tankers joined to the hull plates, metallic members holding helicopter blades aircraft frames, frame support, bridge supports, reactor supports, pressure vessels and the like. All these can fail due to cracking with results catastrophic to the loss of human life and equipment as well as a great loss of productivity.

Crack formation in permeable or porous members subject to stress is also important. For example, in an effort to conserve space and move larger amounts of natural gas, often such materials are liquified and placed in concrete containers which have cryogenic properties much superior to steel or metal containers. Many ships made of concrete have been designed to carry liquified natural gas (LNG) at very low cryogenic temperatures since this is much superior to insulated steel at the temperatures encountered.

In the prior art, various methods have been used to detect initiation and propagation of cracks through material. However, many methods are not subject to use on both porous or non-porous materials. Metallic materials can be checked using magnetic methods. However, this method is not practical for application to permeable or porous and non-magnetic materials in other applications. In addition, such methods are highly dependent upon geometry and cannot be of equal effectiveness in all cases.

Ultrasonic tests have also been employed in the prior art. These methods, however, are surface geometry dependent and require smooth surfaces in order to give an accurate reading. Porous or permeable materials are not adequately inspected by such methods.

The easiest of all methods for detecting cracks is simple visual inspection. Visual inspections were greatly enhanced by applying a substance to the material to be checked removing the substance and then applying a second substance to react with the first to form a dye so that if the first material is oozing from the crack, it is readily apparent. This method is known as the dye-check method, but is not practical when access is limited, such as beneath skins, hull plates, or under water.

U.S. Pat. No. 3,667,862 discloses detecting a crack in the wall of a hollow object by evacuating the interior of the hollow object and detecting loss of vacuum. However, this method is not suitable for detection of cracks existing in non-permeable solid structural members. This method also fails to detect a crack until the crack has completely penetrated the member which is being sensed.

U.S. Pat. No. 2,936,612 teaches a quality factor (Q) which decreases prior to failure by rupture upon increase in the amplitude of dynamic strain for structural members. However, this method is likewise not applicable for the reasons set forth above. U.S. Pat. No. 3,910,224 discloses mounting a fail safe device on members subject to fatigue failure. The fail safe device is made of a material which would fail under fatigue prior to member failure. However, in many instances there is a period of time between such fail-safe failure and the member failure before repairs would necessarily be made. In addition, once the fail-safe material has failed, this method provides no further information as to crack propagation. U.S. Pat. No. 4,135,386 teaches a method for detecting cracks in porous materials by affixing a closed environment "patch" over the area to be tested and detecting loss of such internal atmosphere when a crack propagates into the patch. U.S. Pat. No. 4,143,540 teaches a method for monitoring the integrity of corrosion sheaths to detect penetration of sea water beneath such sheaths by monitoring an ambient atmosphere inside the sheath. However, none of these prior art methods were able to detect initiation and monitor propagation of cracks in all types of materials.

Difficulties arise in using these inspection methods in offshore or underwater applications. Previously used ultrasonic systems, both manual and automatic, are very expensive. This cost includes associated diver time, grinding of a member to permit sensor contact, and the cost associated with installing automatic equipment. In addition, automatic testing cannot handle complex nodes. While ultrasonics have the ability to detect flaws down to approximately 3 millimeters in depth, the probability of finding flaws in the search operation on a large structure decreases in direct proportion to the size of the flaw. In some cases such as aircraft members, cracks are often not available to testing methods. In addition, flaws found by this technique may not have any effect on the integrity of the structure, especially if they are not active or propagating under imposed loads.

Magnetic particle inspection is a second costly technique. Probes used in these inspections must be set as close as possible to the structural member being scanned in order to achieve maximum accuracy and resolution. Marine growth and corrosion products must be ground away. Exterior skins or coverings prohibit use of this method. This method cannot be used on porous materials, and, when useable, is time consuming. In addition, continuous monitoring cannot be done.

The acoustic emission method depends upon the fact that when a material is stressed, plastic deformation and microcracking occurs due to failure. These processes emit high frequency stress waves which can be detected by acoustic instruments such as transducers. The material contains significant defects and yielding will take place at these defects while the bulk of the material is at a low stress level. Yielding or crack propagation at these defects will emit acoustic signals while no emissions will occur from the remainder of the structure. Intensity of emission is related to the stress intensity factor of the crack or flaw. As failure depends on attaining a critical value of the stress intensity factor, the acoustic emissions can be related to the proximity of failure. Thus, the acoustic emission method described in the instant invention has the ability to detect crack initiation, slow or rapid crack growth and the onset of failure. This method allows a continuous span of the material to be monitored without predetermining the precise area for examination and to allow doing so without upsetting operations on operating structures.

In general, systems useful for monitoring the acoustic emitter overlays of the present invention are those currently known in the art for detecting acoustic emissions. Detailed descriptions of such systems can be found in *Machine Design*, Apr. 8, 1976, pages 72–76, and in *Nondestructive Testing*, June 1973, pages 152–158.

Concisely explained, such systems depend on the acoustic event. An acoustic event is generally defined according to particular operating characteristics of the sensing equipment. A threshold level is selected to subdue constantly emitted background noise. This threshold is a voltage threshold set for the acoustic transducers used. Acoustic events exceeding this threshold are measured by peak emission, time from threshold crossing to peak emission, duration of event, and number of cycles (or excursions) beyond the threshold.

For most systems monitoring metallic material, a threshold of 1 volt is normally used. The threshold can be varied depending on required sensitivity, background noise levels, or the energy of the emissions detected for a material.

Thus it is apparent that previous crack detection systems relied upon the capabilities of inspection methods such as diver assisted inspections, magnetic particles, or ultrasonics. These systems all indicate the presence of a crack but do not provide information as to propagation. The witness systems such as the vacuum patch detector provide some information on crack propagation but this is limited only to the initial interception of the crack with the patch. The patch cannot provide further information on propagation after breaking its line of communication such as vacuum or electrical.

Acoustical emission monitoring is a possible inspection method which will resolve these problems. However, it has been reported that the amount of detectable acoustical emission is dependent upon the rolling direction of a structural steel plate. During the life of a welded joint when the fabricated material begins to tear, the propagating crack may not emit acoustically. Additionally, for all classes of materials, including ferrous, nonferrous, cementitious or concrete, and polymeric, there are materials which do not emit or are very poor emitters. It would therefore be of great benefit to provide a means of generating acoustical emissions to detect crack initiation and propagation, such acoustical emission being discernable from background emissions. Such a system would provide detection even when low acoustical emitting conditions are present in the material monitored.

It is therefore an object of the present invention to provide a means for generating acoustical emissions to detect crack formation and propagation. Other objects will become apparent to those skilled in this art as the description proceeds.

We have now discovered a method for detecting and monitoring initiation and propagation of cracks in materials which do not provide a significant acoustical events, comprising (a) adhering an acoustical emitter to the area of the material to be monitored, and (b) monitoring for acoustical signals emitted by the adhered emitter when cracks initiate or propagate into the emitter.

The instant invention is applicable to both structural and non-structural members. The invention is likewise applicable to both porous and non-porous materials. Some materials are inherently acoustical emitters but tend to become low emitters after a crack has initiated and propagated making detection of propagation difficult. Therefore, it is preferred to adhere an acoustical emitter which has a high and dependable level of acoustical emission to the material to be monitored. Among such materials are brittle plastics, epoxies and adhesives, glass rods and strips, fiberglass reinforced materials such as micarta, fiberglass-E, cadmium metal, tin metal, composite reinforced materials such as boron/epoxy reinforced strips, graphite/epoxy laminates or silicon carbide fiber laminates.

These emitters can be adhered to the material by any convenient means. For example, metal can be attached by means of welding, brazing, soldering, or adhesives. Normally, the brittle plastics, glass rods, fiberglass and the like will be adhered by adhesives such as epoxy resins, silicone based adhesives and cyano-acrylate based adhesives.

Generally, sufficient acoustic emission sensors are placed on the structure monitored to receive emissions from all acoustical emitters. A plurality of sensors will be normally connected to a common monitoring system which will record only significant acoustical emissions and will indicate which emitters have produced acoustical energy. Once an emitter has become active, particular care can be made to monitor further crack propagation. Systems are available which will continually record emissions from a given emitter to allow a record of the propagation of each crack through each emitter.

Such emitters would be of great value in aircraft frame members, bridges and offshore platforms in particular. Final failure in such structures is almost always sudden and catastrophic. The present invention allows monitoring and timely repair of crucial fatigued and cracked areas.

The invention is more concretely described with reference to the drawings and examples below. The examples and drawings are provided to illustrate the instant invention and not to limit it.

DETAILED DESCRIPTION OF THE DRAWINGS

Figure 1:
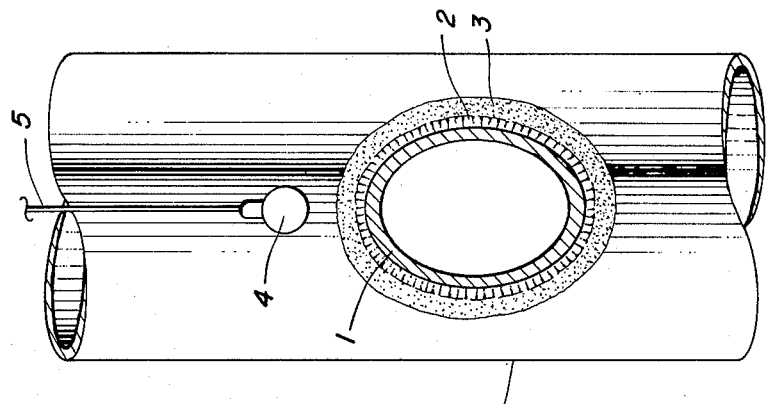
FIG. 1 is a structural joint of an offshore platform showing acoustic emission generating overlays.
Figure 1:
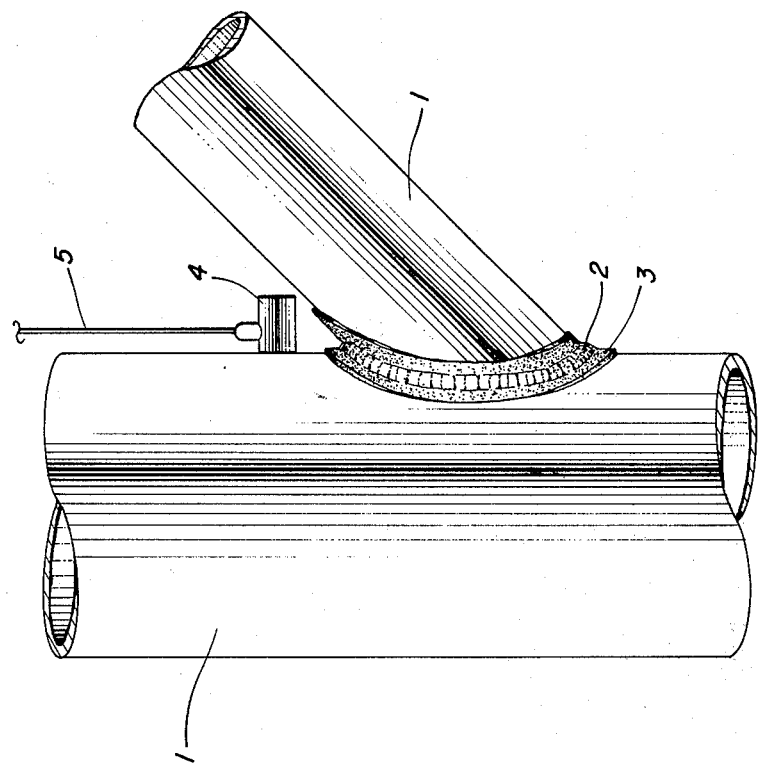

FIG. 1 is a front and side view of a structural joint on an offshore platform, said joint showing an acoustic emission generating overlay attached to the weld or critical area of the joint. Such a material could be any suitable material which emits distinctive acoustical events for purposes of detection. For example, in the drawing the overlay material could be fiberglass or metal adhered by either epoxy for both fiberglass or metal or by welding for metal alone. In the figure, (1) indicates structural members, (2) indicates a structural joint to be monitored, and (3) indicates the overlay material. (4) indicates the transducer to pick up acoustical emissions while (5) is a signal cable which is attached to a system whereby the detected signal is transmitted by electrical means for activating an alarm and/or detector.

Figure 2:
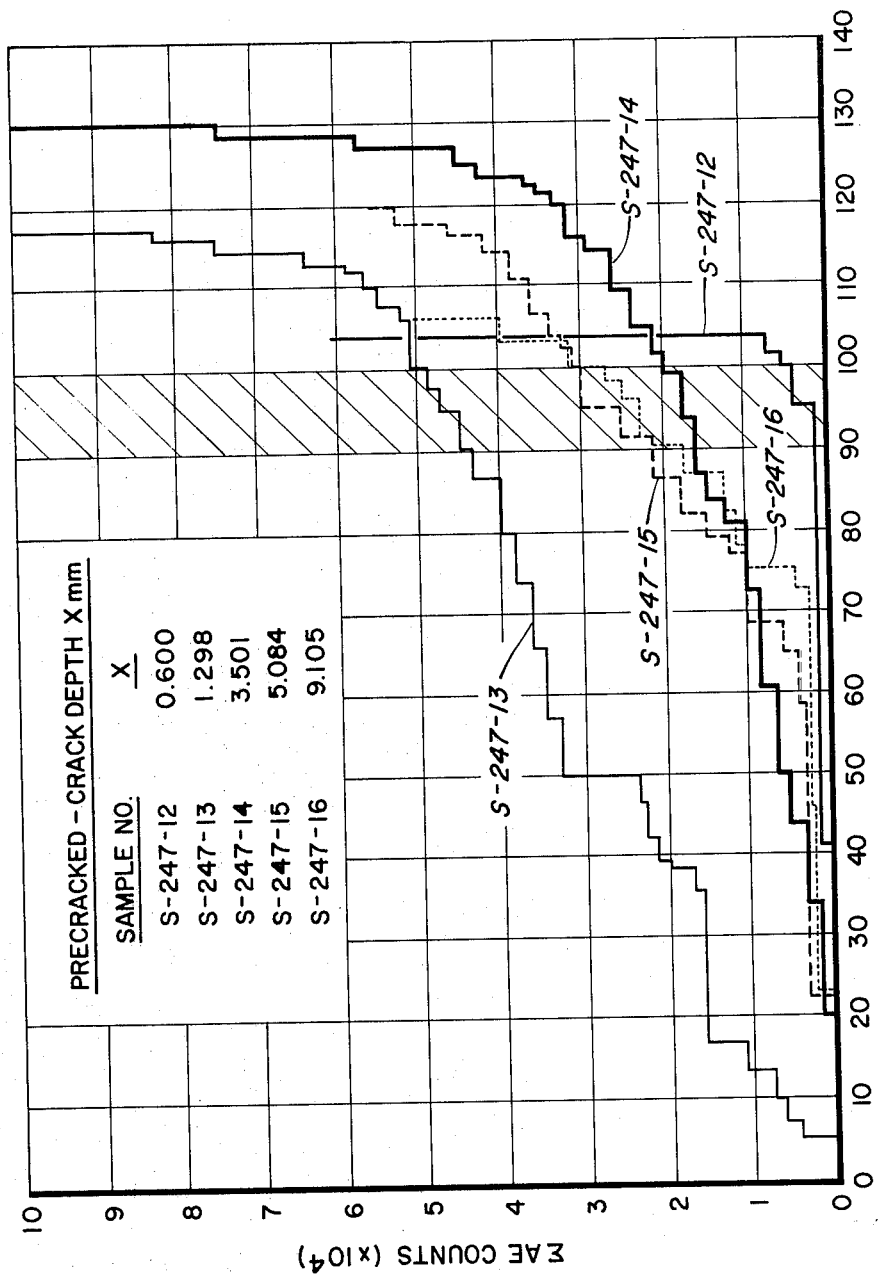
FIG. 2 is acoustic emission response from a drill pipe tool material.

FIG. 2 presents an example of yielding or crack propagation of defects using a drill pipe tool joint material (S247). As failure depends on attaining a critical value and stress intensity factor, ($KI_C$), the acoustic emissions are related to proximity of failure. Thus the figure shows initial crack sizes for the resulting stress intensity value when the pipe was loaded and the crack grew with resulting emission values. The change in slope of accumulative acoustic emission shows a critical stress intensity ($KI_C$) value in a cross hatch region. Once the stress intensity values reach this region the effective service life of the material has been reached. No acoustic emitters were used in these tests since the material itself was an acoustic emitter.

Figure 3:
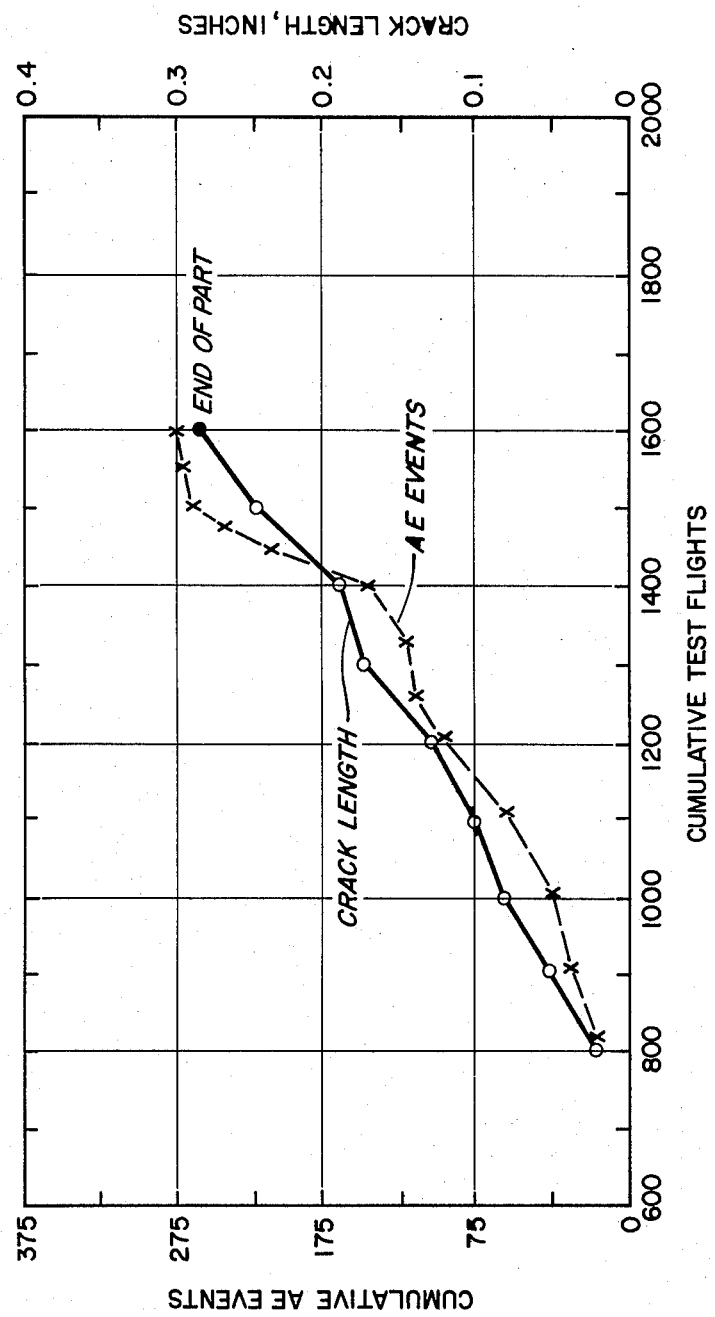
FIG. 3 shows an analysis of correlation between crack growth and cumulative acoustic emission events in an aircraft wing structural material.

FIG. 3 shows the results of an actual example of acoustic emission data collection and interpretation techniques. The data is the result of a fatigue test done on an airplane wing and repeated in Air Force Materials Laboratory Report Ta76214 (December 1976, Wright-Patterson Air Force Base, Dayton, Ohio). This figure shows the accumulative emission and crack growth from a predetermined crack in the wing vs the cumulative test flights. It is apparent that a very good correlation exists between the crack growth and the cumulative acoustic events. No acoustic emitter overlay was used since the material tested in this test is an acoustical emitter.

Figure 4:
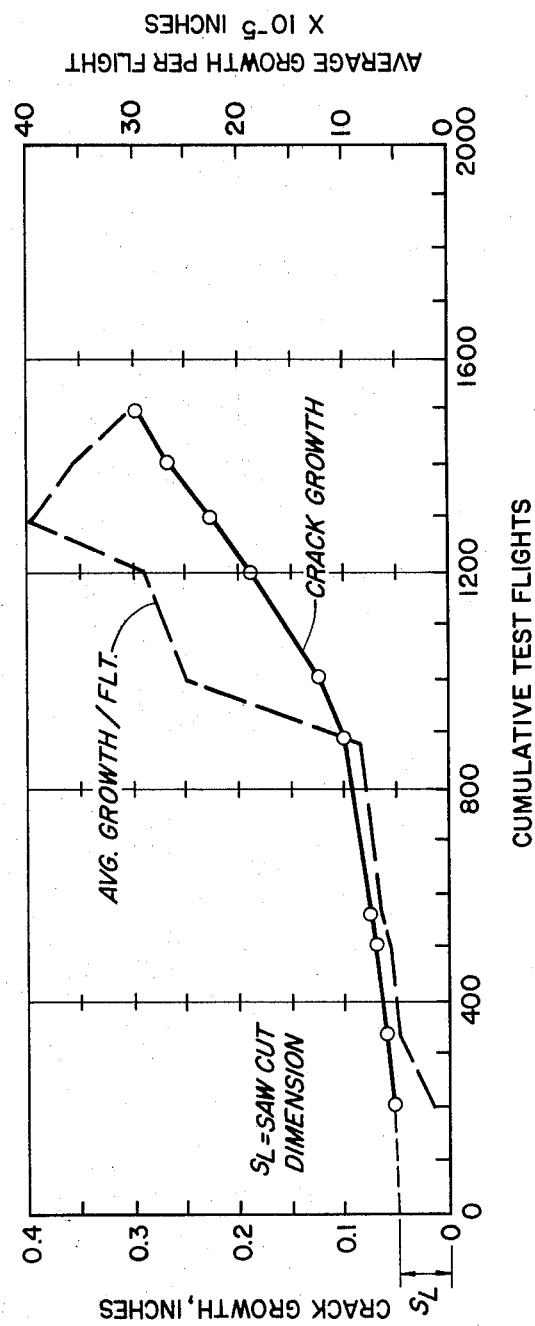
FIG. 4 is an analysis and prediction of crack growth of the data of FIG. 3.

FIG. 4 is an analysis of the data generated using the test events in FIG. 3. From this data a plot of the amount of crack growth per flight was determined as shown in FIG. 4. Thus the time needed to cause a significant crack could be estimated and repairs made prior to failure. This is especially important in view of the increasing age of domestic air flight and number of current crack related problems and accidents on these aircrafts. Using this method the time when it is necessary to repair any defect can be determined by recording accumulative acoustic emission events or crack growth per unit time. In the examples shown in FIG. 4, the crack could be repaired after 1,000 flights but must be repaired after 1,200 flights since the crack is now critical. By relating crack growth to accumulated emissions, the criticality of the crack is evidenced between 1000 and 1200 test flights when the emission slope changes and quickly increases. This is the period when the crack must be repaired. These data show the effectiveness of the instant invention when acoustic emitter overlays are used on low emitting or non-emitting materials. Almost any material can now be monitored by acoustic emission systems.

Thus the instant invention also comprises an apparatus for detecting and monitoring initiation and propagation of cracks in materials comprising (a) an acoustical emitter adhered to the material to be protected, (b) monitoring transducers to detect acoustical signals emitted by the adhered material, and (c) alarm and recording means for notification and recording of signals emitted.

Some materials which would be monitored by the apparatus and method of the instant invention are, in their own regard, acoustic emitters to some extent. Uses of the method of the instant invention in certain applications will require some test results in order to differentiate between the inherent acoustic emissions of the material monitored and those of the emitter placed on the material. Usually, such testing is only minimum required since the acoustic emitter can be chosen as to widely differentiate from the material itself.

While certain embodiments and details have been shown for the purpose of illustrating this invention, it will be apparent to those skilled in this art that various changes and modifications may be made herein without departing from the spirit or scope of the invention.

We claim:

1. A method for detecting and monitoring initiation and propagation of cracks in materials comprising
    (a) adhering an acoustical emitter selected from the group consisting of brittle plastics, glass rods and strips, fiberglass, cadminum metal, tin metal, micarta, boron/epoxy reinforced strips, boron/aluminum reinforced strips, graphite/epoxy laminates and silicon carbide fiber laminates to the area to be monitored, and
    (b) monitoring for acoustical signals emitted by the adhered material, indicating crack initiation or propagation into the adhered material.

2. A method as described in claim 1 wherein the material monitored is a structural material.

3. A method as described in claim 2 wherein the plurality of acoustical emitters are placed on the structural material.

4. A method as described in claim 3 wherein the acoustical emitter is bonded to the structural member with epoxy resins, silicone based adhesives, cyanoacrylate based adhesives, welding, brazing, or soldering.

5. A method as described in claim 4 wherein sensors are placed to receive emissions from all acoustical emitters.

6. A method as described in claim 5 wherein a plurality of sensors are monitored, said monitors being capable of indicating which sensors have been activated.

7. A method as described in claim 6 wherein the monitoring system records activity of each sensor.

8. A method as described in claim 7 wherein the acoustical emitters are placed on an offshore platform.

9. A method as described in claim 7 wherein acoustical emitters are placed on aircrafts.

10. An apparatus for detecting and monitoring initiation and propagation of cracks in material comprising
    (a) an acoustical emitter adhered to the material in the area to be monitored, said emitter selected from the group consisting of brittle plastics, glass rods and strips, fiberglass, cadmium metal, tin metal, micarta, boron/epoxy reinforced strips, boron/aluminum reinforced strips, graphite/epoxy laminates and silicon carbide fiber laminates, (b) a monitor for detecting acoustical signals emitted by the adhered material when cracks in the monitored material initiate or propagate into the acoustical emitter, and (c) a series of transducers placed so as to detect emissions made by the acoustical emitter, said transducer being connected to (d) a monitoring system.

11. An apparatus as described in claim 10 when used on non-porous materials.

12. An apparatus as described in claim 11 when used on structural materials.

13. An apparatus as described in claim 10 when used on porous materials.

14. An apparatus as described in claim 10 wherein the acoustical emitter is adhered to the material to be monitored with epoxy resins, silicone based adhesives, cyanoacrylate based adhesives, brazing, soldering and welding.

15. An apparatus as described in claim 14 wherein a plurality of acoustical emitters are placed on the material monitored.

16. An apparatus as described in claim 15 wherein a common monitoring system which is connected to transducers and is capable of locating the emitter actuated to detect acoustical emissions is used.

* * * * *